United States Patent
Cole et al.

[11] Patent Number: 6,080,132
[45] Date of Patent: Jun. 27, 2000

[54] APPARATUS FOR ALTERING CHARACTERISTICS OF A FLUID

[75] Inventors: Rhonda L. Cole, Powell; Ronita K. Geckle, Columbus; John J. Kropczynski, Jr., Dublin; Terrence B. Mazer, Reynoldsburg; Joseph E. Walton, Westerville, all of Ohio

[73] Assignee: Abbott Laboratories, Abbott Park, Ill.

[21] Appl. No.: 09/032,106

[22] Filed: Feb. 27, 1998

[51] Int. Cl.⁷ .......................... A61M 37/00; A61B 19/00
[52] U.S. Cl. ...................... 604/85; 604/87; 604/414; 604/416
[58] Field of Search .................. 604/80, 81, 82, 604/83, 84, 85, 87, 92, 403, 411, 412, 414, 415, 416, 88, 191; 606/219, 220, 221, 222

[56] References Cited

U.S. PATENT DOCUMENTS

| | | |
|---|---|---|
| 4,390,017 | 6/1983 | Harrison et al. . |
| 4,392,851 | 7/1983 | Elias . |
| 4,511,353 | 4/1985 | Theeuwes . |
| 4,779,722 | 10/1988 | Hall .......................................... 206/221 |
| 4,837,111 | 6/1989 | Deters et al. . |
| 4,839,281 | 6/1989 | Gorbach et al. . |
| 4,927,411 | 5/1990 | Pastrone et al. . |
| 4,968,507 | 11/1990 | Zentner et al. . |
| 4,985,017 | 1/1991 | Theeuwes . |
| 5,069,671 | 12/1991 | Theeuwes ............................... 604/251 |
| 5,092,668 | 3/1992 | Wong et al. . |
| 5,147,646 | 9/1992 | Graham . |
| 5,160,742 | 11/1992 | Mazer et al. . |
| 5,162,057 | 11/1992 | Akiyama et al. . |
| 5,248,310 | 9/1993 | Barclay et al. . |
| 5,318,558 | 6/1994 | Linkwitz et al. . |
| 5,324,280 | 6/1994 | Wong et al. . |
| 5,330,426 | 7/1994 | Kriessel et al. ............................ 604/89 |
| 5,372,578 | 12/1994 | Kriesel et al. . |
| 5,383,579 | 1/1995 | Lanfranconi et al. .................... 222/129 |
| 5,385,545 | 1/1995 | Kriessel et al. ............................ 604/82 |
| 5,385,546 | 1/1995 | Kriesel et al. . |
| 5,385,547 | 1/1995 | Wong et al. . |
| 5,484,410 | 1/1996 | Kriesel et al. . |
| 5,533,647 | 7/1996 | Long-Hsiung ............................ 222/83 |
| 5,533,973 | 7/1996 | Piontek et al. . |
| 5,685,845 | 11/1997 | Grimard .................................... 604/82 |

FOREIGN PATENT DOCUMENTS

| | | |
|---|---|---|
| 059 694 | 9/1982 | European Pat. Off. . |
| 0373890 | 6/1990 | European Pat. Off. . |
| 88/02637 | 4/1988 | WIPO . |
| 9115196 | 10/1991 | WIPO . |
| 9302558 | 2/1993 | WIPO . |
| 96/04038 | 2/1996 | WIPO . |

OTHER PUBLICATIONS

R. G. Potts et al., *Chest*, vol. 103, No. 1, (1993), pp. 117–121.

*Primary Examiner*—Ronald K. Stright, Jr.
*Assistant Examiner*—Patricia M Bianco
*Attorney, Agent, or Firm*—Brian R. Woodworth; Daniel J. Hulseberg

[57] ABSTRACT

An apparatus for altering characteristics of a fluid. The apparatus includes a first perimeter wall defining an internal chamber therein. The first perimeter wall defines a first opening and a second opening therethrough. The first opening is constructed to be fluidly connected to a fluid source. The internal chamber defined in said first perimeter wall is constructed to contain a beneficial agent therein. A beneficial agent is disposed in the internal chamber defined in the first perimeter wall, the beneficial agent being dispersible in a fluid flowing from the first opening to the second opening through the internal chamber defined in the first perimeter wall.

12 Claims, 3 Drawing Sheets

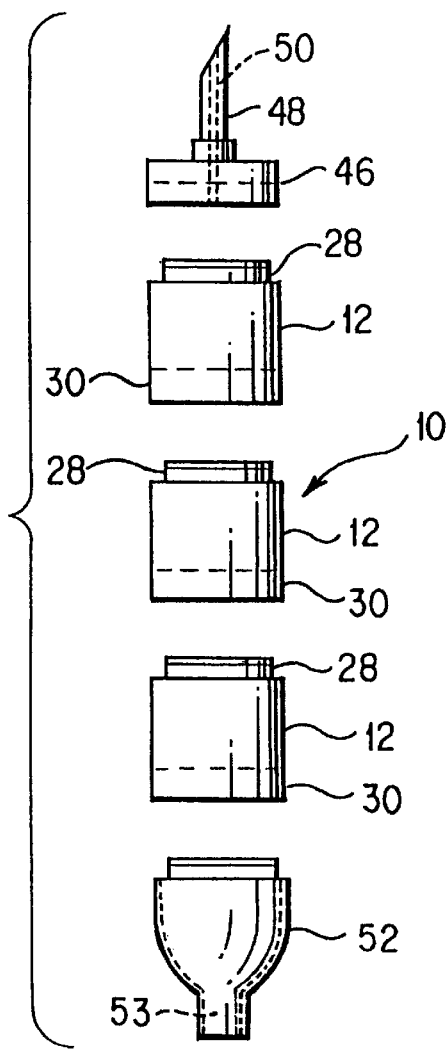
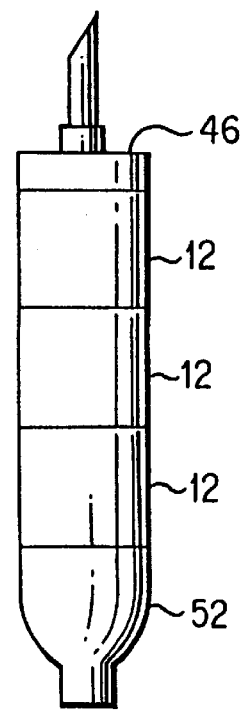
FIG. 1    FIG. 2
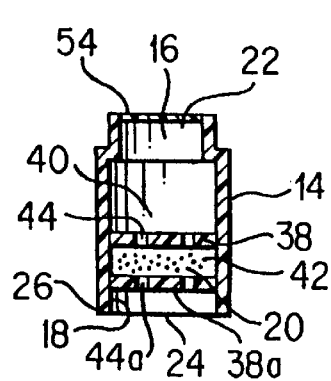
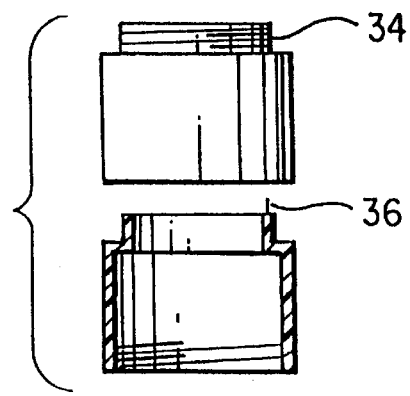
FIG. 3    FIG 4

APPARATUS FOR ALTERING CHARACTERISTICS OF A FLUID

BACKGROUND OF THE INVENTION

The present invention is directed to an apparatus for altering the characteristics of a fluid. In particular, the present invention is directed toan apparatus including a perimeter wall defining an internal chamber constructed to contain a beneficial agent therein. First and second openings are defined through the perimeter wall, thereby defining a fluid flow path through the internal chamber defined by the perimeter wall. A beneficial agent is disposed in the internal chamber, the beneficial agent being dispersible in a fluid flowing through the internal chamber between the first and second openings defined through the perimeter wall.

The delivery of enteral and parenteral products to a patient from a fluid source is well known. Such fluid products can be provided in hangable containers such as bottles and flexible bags having a bottom outlet that is fluidly connected to a drip chamber. The drip chamber in turn is fluidly connected to a flexible tube which in turn delivers the enteral or parenteral product to a patient. For example, an enteral product can be delivered to a patient by way of a nasogastric tube or a feeding tube inserted through a gastrostomy or a jejunostomy while a parenteral product can be delivered by way of a catheter inserted into a patient's vascular system. The parenteral or enteral product is delivered from the container to the patient through the use of gravity or through the use of a pump. Pumps useful in the administration of enteral and parenteral products are well known and include, but are not limited to, rotary peristaltic pumps, piston pumps, and cassette pumps.

Although such parenteral and enteral fluid delivery systems have been used widely in the medical field for many years, they lack a degree of flexibility. That is, in some cases it is desirable to supplement or otherwise alter the contents of enteral or parenteral products with an additional agent or with additional quantities of an agent already contained in the product. Such supplementation or alteration typically requires the use of a specialized delivery system. For example, a piggy-back delivery system can be used in order to provide a bolus of the additional agent to the enteral or parenteral product during administration thereof. Other known sets capable of simultaneously delivering a plurality of fluids from a plurality of sources can be used. However, such systems include additional tubes and ports that can become entangled during use. Further, such systems are typically higher in cost due to the need for additional lengths of tubing and Y-connectors.

Some fluid delivery systems provide for supplementation of the liquid product in a container by providing a port on the container that can be opened, thereby permitting an additional agent, or additional quantities of an agent contained in the product, to be added directly thereto. However, by allowing direct access to the product, the sterility of the product may be compromised during use thereof. In the case of parenteral products, sterility must be maintained during delivery to a patient, thus making direct access unacceptable for parenteral products. The sterility of enteral products historically has posed less of a concern to medical professionals. However, there is a growing recognition of the desirability of providing and delivering aseptic enteral nutritional products to patients. Accordingly, it is desirable to provide a method and apparatus for modifying the characteristics of enteral and parenteral products without exposing the products to contamination.

Without a system or apparatus for easily supplementing the contents of a liquid product prior to delivery thereof from a container to a patient, it becomes necessary to provide products having a wider variety of dosages, volumes, and combinations of agents. For this reason, delivery systems such as those described in U.S. Pat. Nos. 4,511,353; 5,318,558; and 5,324,280 have been developed. In these systems, an agent to be delivered parenterally to a patient is contained in a capsule from which it is ejected over time as a result of osmotic infusion. That is, as the capsule is subjected to the presence of a fluid, the contents of the capsule are released into the fluid. U.S. Pat. No. 5,318,558 discloses the use of such a system in the delivery of agents directly into the body by exposing the capsule directly to bodily fluids.

U.S. Pat. No. 5,069,071 describes a formulation chamber in which various forms of sustained release mechanism can be employed to release agents into a parenteral fluid traversing through the formulation chamber, thereby providing for delivery of the supplemental agent to the patient.

SUMMARY OF THE INVENTION

The present invention provides an apparatus for altering characteristics of a fluid flowing therethrough. The apparatus includes a first perimeter wall defining an internal chamber therein, the first perimeter wall also defining a first opening and a second opening therethrough. The first opening is constructed to be fluidly connected to a fluid source. The internal chamber defined by the first perimeter wall is constructed to contain a beneficial agent therein. A wall is disposed in the internal chamber and divides the internal chamber into upper and lower chambers. beneficial agent is disposed in the internal chamber. The beneficial agent is dispersible in a fluid flowing from the first opening to the second opening, thereby altering the characteristics of such fluid.

BRIEF DESCRIPTION OF THE DRAWINGS

For a more complete understanding of the present invention, reference may be had to the following Detailed Description read in connection with the accompanying drawings in which:

FIG. 1 is an exploded view of a first embodiment of an apparatus constructed in accordance with the present invention;

FIG. 2 is an elevational view of the first embodiment of the apparatus of the present invention;

FIG. 3 is a cross-sectional view of a canister constructed in accordance with the present invention;

FIG. 4 is a partial cross-sectional, exploded view of two canisters constructed in accordance with an alternative embodiment of the present invention;

DETAILED DESCRIPTION

Figure 5:
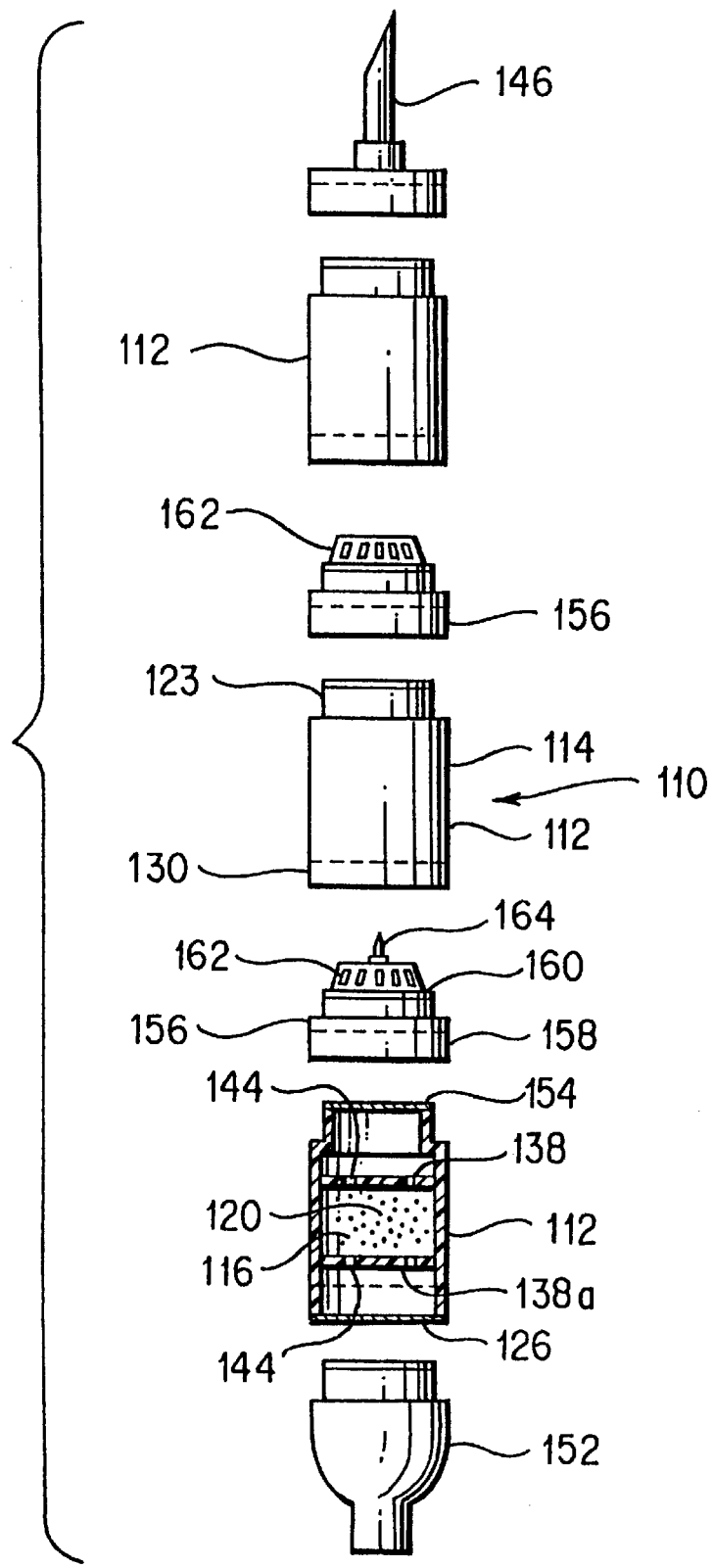
FIG. 5 is an exploded view of a second embodiment of an apparatus constructed in accordance with the present invention.

The present invention is directed to an apparatus and a corresponding method for altering the characteristics of a fluid. For the purposes of this disclosure, the apparatus will be described in the context of an enteral nutritional fluid delivery system. However, it will be appreciated that the present invention also can be used to alter the characteristics of a parenteral fluid as it is delivered to a patient.

The present invention is described herein with reference to the accompanying figures. Terms of reference such as "upper" and "lower" are used to facilitate an understanding of the present invention in view of the accompanying figures. These terms are not intended to be limiting and one of ordinary skill in the art will recognize that the present invention can be practiced in a variety of spatial orientations without departing from the spirit and scope of the present invention.

As used herein, the terms "enteral nutritional product" and "enteral product" refer to a liquid composition designed to be delivered to a patient's gastrointestinal tract. Delivery to the gastrointestinal tract can be effected through a nasogastric tube, through a gastrostomy tube, and/or through a jejunostsomy tube. These liquids typically have a viscosity greater than about 3 centipoises.

A "beneficial agent" is an agent that is, or that is believed to be, nutritionally or pharmaceutically important to the patient, or that is otherwise medically important as in the case of a probiotic, or that serves as a diagnostic agent as in the case of an opaquing agent, an imaging agent, or a coloring agent.

A "probiotic" is understood to be a live microbial food supplement that beneficially affects the human host by improving the microbial balance in the host's gastrointestinal tract, e.g., *Lactobacillus reuteri*.

A "useful amount" of a beneficial agent is an amount that is physiologically effective or diagnostically detectable when administered to a patient or that is believed to be physiologically effective or diagnostically detectable when administered to a patient. That is, an amount that is reasonably expected to produce a detectable effect on the patient on either a short term or long term basis when delivered to the patient or an amount that is detectable in diagnosing a disease state or a medical condition.

"At least one beneficial agent" is meant to refer to the singular as well as the plural and is intended to include combinations of ingredients, agents, or factors.

The term "dispersible" as used herein with respect to beneficial agents is to be understood to apply to substances that are soluble as well as those that are suspendable enough to be taken up readily and carried along by the liquid medium as the liquid flows through the chamber containing the beneficial agent. Dispersible agents include, but are not limited to, agents in controlled release dosage form.

The term "feeding set" refers to a combination of known elements useful in delivering a product from a liquid container to a patient. Such combinations include, but are not intended to be limited to, combinations comprising one or more of drip chambers, formulation chambers, lengths of tubing, flow control clamps, pumps, and other devices commonly found in infusion sets.

The term "infusion" is meant to refer to the enteral or parenteral delivery of a liquid to a patient.

The term "controlled release dosage form" refers to any known or conventional controlled release form, including coated tablets, osmotic delivery devices, coated capsules, microencapsulated particles such as microspheres, agglomerated particles, e.g., molecular sieve particles, or a fine, hollow, permeable-walled fiber. Each of these forms contains and subsequently releases or disperses a beneficial agent. Such forms preferably prolong the release of the beneficial agent into the liquid.

The term "controlled release dosage form unit" refers to individual coated tablets or coated capsules or devices such as osmotic delivery devices or microcapsule particles or small bundles of fine hollow fibers or small agglomerated clumps of molecular sieving type material, each being capable of sustained delivery or delayed or intermittent delivery of beneficial agent therefrom.

The term "flowing the liquid" is intended to include the utilization of gravity to effect flow as well as using a pump of known construction to effect flow.

An apparatus 10 constructed in accordance with the present invention is generally depicted in the accompanying figures. Apparatus 10 includes one or more canisters 12. Canister 12 includes perimeter wall 14 which defines an internal chamber 16 therein. The shape and size of canister 12, perimeter wall 14, and internal chamber 16 can be varied without affecting their utility in connection with apparatus 10 and method of the present invention. However, interior surface 18 of perimeter wall 14 preferably is configured such that it does not impede the flow of a liquid therethrough. Further, internal chamber 16 preferably is of a size and shape that is conducive to the placement of a desired quantity of a beneficial agent 20 therein. In connection with the present invention, beneficial agent 20 can have a variety of forms, including, but not limited to, powders, gels, agglomerations, tablets, and other controlled release dosage form units.

Perimeter wall 14 defines first opening 22 and second opening 24. In the embodiment of the present invention depicted in the accompanying figures, canister 12 is substantially cylindrical in shape. First opening 22 and second opening 24 can be positioned in a variety of locations on canister 12. However, in the preferred embodiment, first opening 22 and second opening 24 are positioned at opposite ends of perimeter wall 14, thereby facilitating flow through canister 12. In the preferred embodiment, first opening 22 and second opening 24 are each coaxial with a longitudinal axis of canister 12.

Membrane 26 is provided in order to prevent the premature passage of beneficial agent 20 outwardly from internal chamber 16 through second opening 24. Membrane 26 can be placed over second opening 24 such that membrane 26 is in physical contact with an exterior surface of perimeter wall 14, as depicted in FIG. 3. Alternatively, membrane 26 can be placed within internal chamber 16 at a position proximate to second opening 24 such that membrane 26 is in physical contact with interior surface 18 of perimeter wall 14. The reason that membrane 26 is positioned proximate to second opening 22, as well as the preferred spacing between membrane 26 and second opening 22, will be explained in detail below.

Membrane 26 can be constructed of a variety of known materials that prevent that egress of beneficial agent 20 from internal chamber 16. Membrane 26 can be constructed of either a fluid tight or a fluid pervious material. However, in the preferred embodiment of the present invention, membrane 26 is constructed of a material that provides a substantially fluid-tight seal between internal chamber 16 and an external environment of canister 12, thereby preventing the ingress and/or egress of particulate and/or liquid between internal chamber 16 and an exterior environment of canister 12 through second opening 24 when membrane 26 is in place. Also in the preferred embodiment, membrane 26 is constructed of a frangible material that can be pierced or otherwise broken or dislodged when used in connection with apparatus 10 of the present invention, as discussed in detail below. Examples of materials that can be used to construct membrane 26 include, but are not limited to, plastic films, foils, papers, and coated papers.

First end portion 28 of canister 12 preferably is configured such that it can be mechanically connected to second end portion 30 of a second canister 12. First end portion 28 of a first canister 12 and second end portion 30 of a second canister 12 preferably are constructed such that they can be connected to each other in a manner that provides a substantially fluid-tight seal therebetween, i.e., a seal that does not allow the ingress or egress of fluid between internal chambers 16 of the respective canisters 12 and an external environment of the respective canisters 12. For example, in one embodiment of the present invention, an external dimension of first end portion 28 is selected such that first end portion 28 can be frictionally retained by interior surface 18 of perimeter wall 14 at second end portion 30. In the embodiment of the present invention depicted in FIG. 1, a shoulder is defined on interior surface 18 in order to effect the desired connection between first and second canisters 12. In this way, a plurality of canisters 12 can be interconnected by frictionally retaining a first end portion 28 of a second canister 12 within a second end portion 30 of a first canister 12.

In an alternative embodiment of the present invention, first thread 32 is formed on interior surface 18 of perimeter wall 14 proximate to second end portion 30. Complementary second thread 34 is formed on an exterior surface of perimeter wall 14 proximate to first end portion 28. First thread 32 and second thread 34 are positioned such that they threadably secure a first end portion 28 of a second canister 12 to a second end portion 30 of a first canister 12 upon relative rotation therebetween. In this embodiment, first end portion 28 of a second canister 12 is constructed such that it is received in second end portion 30 of a first canister 12.

It will be appreciated that membrane 26 will tend to interfere with the placement of first end portion 28 of a second canister 12 into second end portion 30 of a first canister 12. However, as above, discussed, membrane 26 preferably is constructed of a frangible material or is otherwise mounted on canister 12 such that it becomes pierced or dislodged upon the insertion of first end portion 28 of a second cannister 12 into second end portion 30 of a first cannister 12, thereby placing internal chambers 16 of the first and second canisters 12 in fluid communication with one another. The requisite tearing or dislodgement of membrane 26 can be effected by perimeter wall 14 of a second canister 12 as first end portion 28 thereof is urged into second end portion 30 of a first canister 12. It will be appreciated that if membrane 26 is positioned as depicted in FIG. 3, membrane 26 will become pierced, torn, or dislodged as first end portion 28 of a second canister 12 is urged therethrough. However, if membrane 26 is positioned within internal chamber 16 of canister 12, the position of membrane 26 and the construction of first end portion 28 will need to be selected such that the requisite piercing, tearing, or dislodgement of membrane 26 occurs. The spacing between membrane 26 and second opening 24 thus is no greater than the distance that first end portion 28 of second canister 12 extends into second end portion 30 of first canister 12 when the canisters 12 are physically connected to one another.

The piercing of membrane 26 can be facilitated by piercing member 36 mounted on first end portion 28 of canister 12. Piercing member 36 preferably is constructed such that it pierces membrane 26 when two canisters 12 are urged into physical engagement with one another. Piercing member 36 also is preferably constructed such that it creates an arced tear in membrane 26 as a first canister 12 is rotated relative to a second canister 12. It will be appreciated that an arced tear in membrane 26 will be created by relative rotation between adjacent canisters 12 regardless of whether the canisters 12 are connected by a frictional fit, by complementary threads, or by some other known method for mechanically connecting adjacent canisters 12.

Second membrane 54 preferably is provided in order to seal first end portion 28 of canister 12, thereby preventing the egress of beneficial agent 20 from internal chamber 16. As above-discussed with respect to membrane 26, second membrane 54 can be constructed of a variety of materials. In the preferred embodiment of the present invention, second membrane 54 is constructed of a material that prevents the egress of beneficial agent 20 and fluids from canister 12 as well as presenting the ingress of particulate and fluids into internal chamber 16 from an exterior environment of canister 20.

Second membrane 54 can be constructed to be removed from first end portion 28 of canister 12. That is, second membrane 54 can include an adhesive backing that permits second membrane 54 to be peeled from first end portion 28 of canister 12 prior to use of canister 12. It will be appreciated that membrane 26 also can be provided with an adhesive backing that permits it to be peeled from canister 12. However, in the preferred embodiment of the present invention, membrane 26 is pierced, torn, or dislodged rather than being removed completely from canister 12.

In a second embodiment, second membrane 54 is constructed of a frangible web material that can be pierced by a piercing member. This embodiment of the present invention will be described in greater detail in connection with the alternative embodiments of the present invention.

Wall 38 is positioned within internal chamber 16 such that it divides internal chamber 16 into upper chamber 40 and lower chamber 42. It will be appreciated that the relative sizes of upper chamber 40 and lower chamber 42 do not affect the utility of apparatus 10 of the present invention. Wall 38 preferably defines one or more apertures 44 therethrough. The number, size, and location of apertures 44 will be selected based upon a variety of factors including, but not limited to, the form of the beneficial agent (e.g., powder, granular, tablet, etc.), the characteristics of the liquid to be flowed through canister 12, and the desired flow characteristics through canister 12 with respect to beneficial agent 20. The size of apertures 44 preferably is selected so as to minimize or prevent the flow of particles of beneficial agent 20 therethrough. However, the size of apertures 44 preferably is selected such that liquid having beneficial agent 20 dispersed therein will pass through wall 38 and into a patient.

Beneficial agent 20 can be disposed above or below wall 38. In the event that beneficial agent 20 is placed below wall 38, beneficial agent 20 will be retained between wall 38 and membrane 26. However, it is preferred that beneficial agent 20 be placed above wall 38 when only one wall is positioned within internal chamber 16.

In the event that multiple canisters 12 are used simultaneously, walls 38 will prevent beneficial agents 20 in respective canisters 12 from coming into direct contact with one another unless they are dispered in a liquid flowing through the plurality of canisters 12. That is, each wall 38 will prevent beneficial agent 20 from the canister 12 immediately above it from coming into contact with beneficial agent 20 contained therein.

In the preferred embodiment of the present invention, wall 38a is positioned within internal chamber 16 at a positioned spaced from wall 38. In this embodiment, beneficial agent 20 is positioned between wall 38 and wall 38a. Wall 38a preferably defines one or more apertures 44a therethrough. The number, size, and location of apertures 44a will be selected based upon a variety of factors, as above-discussed. In this embodiment, beneficial agent 20 will be retained in its original canister 12 between walls 38, 38a until it becomes dispersed in a liquid flowing through the canister. Walls 38, 38a further prevent the migration of beneficial agent between canisters 12 until beneficial agent 20 has become dispersed in a liquid traversing through canisters 12.

Apparatus 10 of the present invention further includes member 46 constructed to fluidly attach apparatus 10 to a source of a liquid. In the embodiment of the present invention depicted in the accompanying figures, member 46 is in the form of a spike 48 of known construction. Spike 48 defines channel 50 therethrough. Spike 48 is constructed such that it can be mechanically connected to an uppermost canister 12 of apparatus 10. For example, spike 48 can be configured such that it frictionally retains uppermost canister 12 therein, as above-discussed with respect to adjacent canisters 12. Alternatively, spike 48 and uppermost canister 12 can be provided with complementary threads which allow spike 48 to be threadably secured to canister 12, also as above-discussed with respect to adjacent canisters 12.

In an alternative embodiment of the present invention, member 46 is constructed to provide fluid communication between uppermost canister 12 and another portion of a fluid delivery set. For example, member 46 can be constructed to connect fluidly to a drip chamber or to a piece of tubing used in a fluid delivery set, thereby allowing an operator to connect one or more canisters 12 in-line with the fluid delivery set. In this embodiment, member 46 can be connected to a portion of the fluid delivery set using a variety of known techniques, e.g., luer or locking luer connections.

Apparatus 10 further includes outlet member 52. Outlet member 52 is constructed to connect fluidly the lowermost canister 12 with a fluid set for delivering an altered liquid to a patient. Outlet member 52 can be constructed to be mechanically connected to a drip chamber, to a length of tubing, or to any other apparatus for delivering liquid enterally or parenterally to a patient. Outlet member 52 defines a channel 53 therein which allows liquid to pass from canister 12 connected to outlet member 52 into a drip chamber, length of tubing, or other apparatus for delivering the liquid to a patient. Outlet member 52 can be frictionally or threadingly secured to canister 12, as above-discussed. Outlet member 52 can be connected to other portions of a fluid delivery set using known techniques, e.g, a luer or locking luer connection.

Use of apparatus 10 of the present invention will now be described. One or more canisters 12 are provided. The number of canisters used will be contingent upon both (a) the volume of a single beneficial agent to be delivered to the patient; and (b) the number of separate beneficial agents to be delivered to the patient. It will be appreciated that each canister can contain one or more beneficial agents and that each beneficial agent can be in a variety of forms, e.g., powder, granular, tablet, or controlled release dosage form. If more than one canister 12 is to be used, the canisters 12 are mechanically connected to one another such that a first end portion 28 of one canister 12 is inserted into a second end portion 30 of another canister 12. In the event that second membrane 54 is present on first end portion 28 of canister 12, it is necessary for second membrane 54 to be removed or otherwise penetrated prior to the interconnection of adjacent canisters 12. As above-discussed, second membrane 54 can be constructed such that it can be peeled from first end portion 28 of canister 12, thereby providing access to internal chamber 16 defined by canister 12.

As above-discussed, the mechanical connection of one canister to another will cause the perforation or dislodgement of membrane 26 positioned at second end portion 30 of canister 12. This effect can be caused by perimeter wall 14 or by piercing member 36. Upon the removal of second membrane 54 and the perforation or dislodgement of membrane 26, flow of liquid through internal chamber 16 will be possible. As liquid is flowed through internal chamber 16, beneficial agent 20 therein will become dispersed in the liquid and thereafter delivered to the patient.

The uppermost canister 12 is physically connected in series with a fluid delivery set by way of member 46. The lowermost cannister 12 is physically connected in series with a fluid delivery set by way of outlet member 52 as above-discussed. Apparatus 10 is depicted in its assembled form in FIG.2 . Upon assembly, the fluid delivery set will include one or more canisters 12, such canisters being in series with the remainder of the fluid delivery set. That is, internal chambers 16 form a portion of the flow path of the fluid delivery set. Thus, liquid flowed through the fluid delivery set and canisters will have the selected beneficial agents dispersed therein. Again, it will be appreciated that apparatus 10 of the present invention allows great latitude in the number and volume of beneficial agents 20 delivered to the patient.

Beneficial agents 20 can be provided in a variety of forms. For example, a powdered beneficial agent can be used in connection with the present invention. Beneficial agent 20 also can be in a granular form or tablet form. Other forms of beneficial agent 20, including, but not limited to, dosage form units, can be used. The particular form of each beneficial agent 20 used in connection with the present invention will be selected based upon the desired delivery profile of the beneficial agents 20 to the patient.

An alternative embodiment of the present invention is depicted in FIG. 5. As depicted in FIG. 5, apparatus 110 of the present invention includes one or more canisters 112. Each canister 112 includes a perimeter wall 114 defining an internal chamber 116 therein. In this embodiment of the present invention, walls 138, 138a are positioned in internal chamber 116 such that a beneficial agent 120 can be contained therebetween. As above-discussed, the apparatus of the present invention will function if only one wall 138 is provided. In particular, if beneficial agent 120 is in a tablet or unit dose form, one of wall 138 and wall 138a may not be necessary to prevent the egress of beneficial agent 120 from internal chamber 116 prior to the juncture at which beneficial agent 120 becomes dispersed in a liquid flowing through canister 112. However, the preferred embodiment of the present invention utilizes both walls 138 and 138a. Walls 138, 138a preferably define apertures 144 therethrough, thereby allowing the flow therethrough of a liquid having beneficial agent 120 dispersed therein.

Membrane 126 is positioned such that it seals second end portion 130 of canister 112. Membrane 126 is constructed in accordance with the discussion set forth above with respect to membrane 26. Second membrane 154 is positioned such that it seals first end portion 128 of canister 112. Second membrane 154 is constructed in accordance with the discussion set forth above with respect to second membrane 54.

Collar 156 is provided and is constructed to interconnect successive canisters 112. Collar 156 includes a first end portion 158 constructed such that first end portion 128 of a canister 112 can be mechanically connected thereto by way of a frictional fit, threading engagement, or other known mechanical connection technique. Collar 156 further includes a second end portion 160 constructed to be mechanically connected to a second end portion 130 of a first canister by way of a frictional fit, threading engagement, or other known mechanical connection technique. Collar 156 defines a fluid flow path therethrough.

Second end portion 160 includes apertured member 162. Apertured member 162 defines one or more apertures therethrough and is positioned transversely across collar 156, thereby limiting flow through collar 156. The size, number, and position of the apertures will be determined by the type of beneficial agent 120 contained in each canister 120 as well as by the desired flow characteristics through collar 156 and canisters 112. However, apertured member 162, and the apertures defined thereby, are constructed such that liquid having one or more beneficial agents 120 dispersed therein can flow therethrough from a first canister 112 to a second canister 112. Apertured member 162 further limits the ability of beneficial agent 120 to move from one canister 112 to a second canister 112.

Second end portion 160 further includes a piercing member 164 constructed to penetrate membrane 126 as second end portion 160 is urged into physical engagement with second end portion 130 of a first canister 112. Piercing member 164 can have a variety of known configurations suitable for piercing membrane 126. In one embodiment of the present invention, an upper edge of apertured member 162 is constructed to provide the desired piercing of membrane 126 as collar 156 and canister 112 are urged into physical engagement with one another. In this embodiment, the upper edge of apertured member 162 serves as piercing member 164. In a second embodiment depicted in FIG. 5, piercing member 164 is a separate member extending outwardly from the upper edge of apertured member 162. Piercing member 164 preferably is constructed to both pierce and tear membrane 126, thereby allowing a person using apparatus 110 to form a single hole through membrane 126 or to tear an arced opening in membrane 126 by effecting relative rotational movement between adjacent canisters 112.

The embodiment of the present invention depicted in FIG. 5 further includes member 146 and outlet member 152 constructed in accordance with the discussion set forth above with respect to member 46 and outlet member 52, respectively.

Use of the embodiment of the present invention depicted in FIG. 5 will now be described. One or more canisters 112 containing one or more beneficial agents are provided. In addition, collars 156 are provided, the number of collars being one less than the number of canisters 112 that are to be interconnected. Second membrane 154 is removed from a first canister 112 and a first end portion 158 of a first collar is urged into physical engagement with first end portion 128 of first canister 112. Second end portion 130 of a second canister 112 is then urged into physical engagement with second end portion 160 of the first collar 156. As second canister 112 is urged into physical engagement with the first collar 156, apertured member 162 of the first canister 156 is urged into the second canister 112 and piercing member 164 pierces membrane 126, thereby placing the first and second canisters 112 in fluid communication with one another through collar 156.

The number of canisters 112 interconnected in this manner will be determined by the number and volume of beneficial agents 120 to be delivered to the patient. The number of collars 156 required will be one less than the number canisters to be interconnected.

Outlet member 152 is urged into physical engagement with second end portion 130 of the first canister 112. As outlet member 152 is urged into physical engagement with the first canister 112, membrane 126 will be pierced by outlet member 152, thereby providing fluid communication between the first canister 112 and outlet member 152. As above-discussed, outlet member 152 can be constructed for fluid connection to a variety of known fluid delivery sets.

Member 146 is urged into physical engagement with first end portion 128 of the uppermost canister 112. It will be appreciated that liquid flowing through member 146 and into the uppermost canister 112 will flow through each of the canisters 112 interconnected by collars 156, thereby exposing each beneficial agent contained in each of the canisters 112 to come into contact with the liquid and thereupon become dispersed in the liquid. Thus, liquid exiting the first canister through outlet member 152 will have dispersed therein each of the beneficial agents 120 contained in each of the canisters 112, unless one or more of the beneficial agents 120 are in a sustained release form, in which case the beneficial agent 120 in sustained release form will be dispersed in the flowing liquid at a subsequent time.

Figure 6:
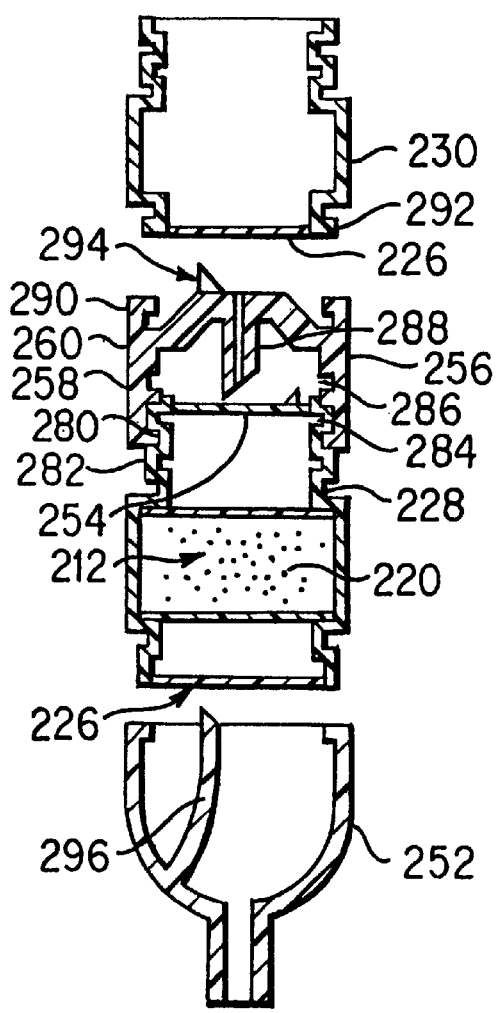
FIG. 6 is an exploded view of a third embodiment of an apparatus constructed in accordance with the present invention.

In another embodiment of the present invention depicted in FIG. 6, canister 212 is constructed to receive collar 256 thereon. Collar 256 can be mechanically mounted on canister 212 using a variety of known techniques. For example, collar 256 can be threadably secured to canister 212 through the use of complementary threads formed on collar 256 and canister 212. In the embodiment of the invention depicted in FIG. 6, canister 212 includes first shoulder 280 and second shoulder 282 on first end portion 228 thereof. First shoulder 280 and second shoulder 282 are constructed to retain frictionally collar 256 in a first position and in a second position, respectively.

Collar 256 includes a first shoulder 284 and second shoulder 286 on first end portion 258 thereof. First shoulder 284 and second shoulder 286 are constructed to be complementary with first shoulder 280 and second shoulder 282 on canister 212 such that collar 256 can be retained frictionally on canister 212 in first and second positions, as above-discussed. Collar 256 further includes a first piercing member 288. First piercing member 288 is constructed to pierce second membrane 254 on canister 212. First piercing member 288 is in the form of a spike defining a flow path therethrough in the embodiment of the invention depicted in FIG. 6. However, it will be appreciated that first piercing member 288 can have a variety of forms, including, but not limited to, piercing pins and pierce/plow members, so long as it is constructed to pierce second membrane 254 so as to provide fluid communication between adjacent canisters 212. First piercing member 288 also can be constructed such that it will provided an arced tear in second membrane 254 when relative rotation is provided between collar 256 and canister 212.

Figure 7:
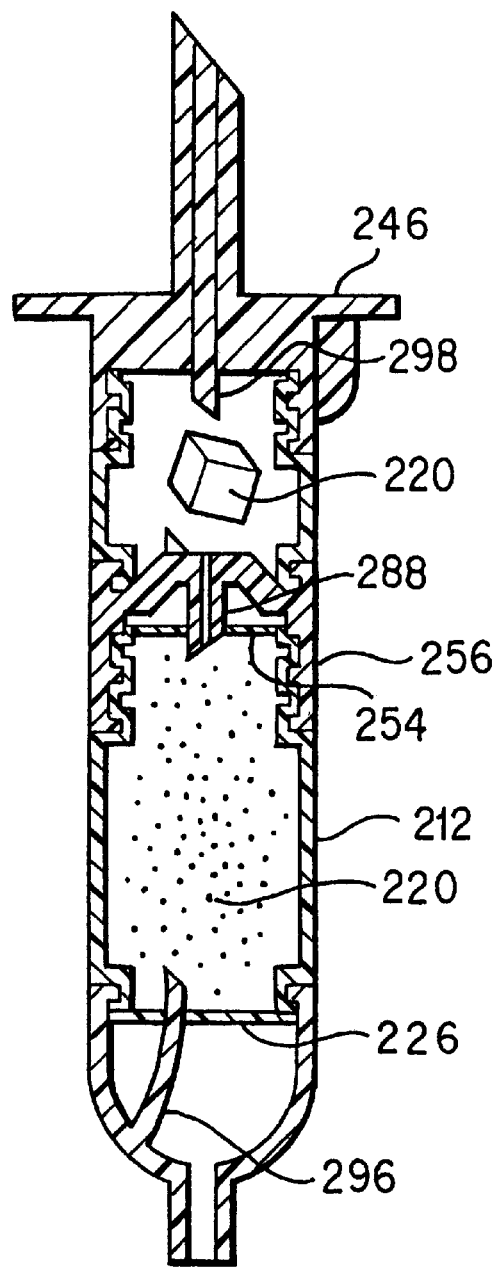
FIG. 7 is an elevational view of the third embodiment of the apparatus of the present invention.

When collar 256 is in its first position attached to canister 212, as depicted in FIG. 6, first piercing member 288 remains spaced from second membrane 254, thus allowing second membrane 254 to prevent the egress of beneficial agent 220 and fluid from canister 212. Second membrane 254 also prevents the ingress of fluids into canister 212. However, when collar 256 is moved to its second positioned attached to canister 212, as depicted in FIG. 7, first piercing member 288 will penetrate second membrane 254, thereby providing fluid access between a flow path defined by collar 256 and internal chamber 216 of canister 212.

Collar 256 further includes a third shoulder 290 on second end portion 260 thereof. Third shoulder 290 is constructed to be complementary with third shoulder 292 defined by on second end portion 230 of canister 212 such that collar third shoulder 290 and canister third shoulder 292 will interlock so as to mechanically connect second end portion 230 of canister 212 to second end portion 260 of canister 212. Collar 256 also includes second piercing member 294 on second end portion 260 thereof. Second piercing member 294 is constructed to pierce membrane 226 on second end portion 230 of canister 212 as canister 212 is mechanically connected to collar 256 by way of collar third shoulder 290 and canister third shoulder 292. Upon the piercing of membrane 226 by second piercing member 294 and the piercing of second membrane 254 by first piercing member 288, two canisters 212 will be connected to one another by way of a single collar 256. Fluid flow through each of the canisters 212 and the collar 256 thus is possible.

In the embodiment of the invention depicted in FIG. 6, outlet member 252 includes a piercing member 296 which is constructed to pierce membrane 226 on the lowest canister 212. Outlet member 252 is constructed to be mechanically connected to the lowest canister 212 by way of a threading or frictional connection. Piercing member 296 is positioned such that it pierces membrane 226 as lowest canister 212 is mechanically connected to outlet member 252, thereby providing fluid communication between the lowest canister 212 and outlet member 252.

Member 246 includes a piercing member 298 which is constructed to pierce second membrane 254 of the uppermost canister 212. Member 246, as above-discussed, is constructed to be mechanically connected to the uppermost canister 212 by way of a threading or frictional connection. Piercing member 298 is positioned such that it pierces membrane 254 of the uppermost canister 212 as the uppermost canister 212 is mechanically connected to member 246, thereby providing fluid communication between member 246 and internal chamber 216 of the uppermost canister 212.

Use of the embodiment of the present invention depicted in FIG. 6 will now be explained. One or more canisters 212 containing the selected type and amount of beneficial agent (s) 220 are provided. Collars 256 are also provided, the number of collars being one less than the number of canisters 212 provided. Adjacent canisters 212 are interconnected by a collar 256 such that fluid communication is established between adjacent canisters 212, as above-discussed. The uppermost canister 212 is connected to member 246 which in turn can be connected to a supply of a liquid. The lowermost canister 212 is connected to outlet member 252 which in turn can be connected to a fluid set for delivery of a liquid to a patient. Liquid introduced into member 246 thus will flow through each of the canisters 212, thereby contacting each of the beneficial agents 220 contained therein. As the liquid comes into contact with beneficial agents 220, the beneficial agents 220 will become dispersed therein and subsequently delivered to the patient with the liquid.

It will be appreciated that a variety of mechanisms can be used for interconnecting canisters with collars in accordance with the embodiments of the present invention depicted in FIGS. 5–7. In this regard, it is important that the resulting connection provides a substantially fluid-tight seal, thereby preventing the flow of fluid into or out of the flow path defined by the canisters 212 and collars 256. If the resulting flow path is not fluid-tight, air will be drawn into the fluid path as liquid passes therethrough, thereby making it difficult, if not impossible, to deliver the liquid from a fluid source to a patient.

Although the present invention has been described herein in connection with certain preferred embodiments, one of ordinary skill will appreciate that various modifications are possible without departing from the intended spirit and scope of the invention which is defined by the appended claims.

What is claimed is:

1. An apparatus for altering characteristics of a fluid, said apparatus comprising:

a first canister including
a first perimeter wall defining first internal chamber therein, said first perimeter wall defining a first opening and a second opening therethrough, said first opening constructed for fluid connection to a fluid source;

a second canister including
a second perimeter wall defining a second internal chamber therein, said second perimeter wall defining a first opening and a second opening therethrough, said second canister constructed to be mechanically connected to said first canister, said first and second perimeter walls defining a flow path therethrough from said first opening defined through said first perimeter wall to said second opening defined through said second perimeter wall when said first canister and said second canister are mechanically connected together;

at least one of said first internal chamber and said second internal chamber constructed to contain a beneficial agent therein; and a beneficial agent disposed in said internal chamber that is constructed to contain the beneficial agent, said beneficial agent being dispersible in a fluid flowing from said first opening of the first canister to said second opening of said second canister.

2. An apparatus for altering characteristics of a fluid in accordance with claim 1, wherein the beneficial agent is disposed in said first internal chamber, said apparatus further comprising:

a frangible membrane covering said second opening defined through said first perimeter wall, said frangible membrane constructed to retain said beneficial agent in said first internal chamber.

3. An apparatus for altering characteristics of a fluid in accordance with claim 2, wherein said apparatus further comprises:

a piercing member mounted on said second canister proximate said first opening defined through said second perimeter wall, said piercing member constructed to pierce said frangible membrane covering said second opening defined through said first perimeter wall when said first and second canisters are mechanically connected together.

4. An apparatus for altering characteristics of a fluid in accordance with claim 1, wherein said first perimeter wall defines a first thread thereon and said second perimeter wall defines a second thread thereon, said first and second threads being complementary to mechanically connect said first and second canisters together.

5. An apparatus for altering characteristics of a fluid in accordance with claim 1, wherein said first perimeter wall and said second perimeter wall are constructed to be snap fit to one another to mechanically connect said first and second canisters together.

6. An apparatus for altering characteristics of a fluid in accordance with claim 1, wherein said apparatus further comprises:

a spike constructed to be mounted on said first perimeter wall, said spike defining a channel therethrough for fluid communication with said first internal chamber through said first opening defined through said first perimeter wall when the spike is mounted thereon, said spike constructed to pierce a pierceable seal of a fluid source.

7. An apparatus for altering characteristics of a fluid in accordance with claim 1, wherein said second canister is constructed to be connected to an apparatus for delivering fluid to a patient.

8. An apparatus for altering characteristics of a fluid in accordance with claim 1, wherein said internal chamber that is constructed to contain a beneficial agent includes a transverse wall having at least one aperture therethrough to divide said internal chamber that is constructed to contain a beneficial agent into separate chamber portions.

9. An apparatus for altering characteristics of a fluid, said apparatus comprising:

a first canister having a first perimeter wall, said first perimeter wall defining a first internal chamber therein, said first internal chamber constructed to contain a beneficial agent therein, said first perimeter wall defining first and second openings therethrough;

a frangible membrane covering said second opening defined through said first perimeter wall of said first canister;

a first beneficial agent disposed in said first internal chamber defined by said first perimeter wall of said first canister;

a second canister having a second perimeter wall, said second perimeter wall defining a second internal chamber therein, said second internal chamber constructed to contain a second beneficial agent therein, said second perimeter wall defining first and second openings therethrough;

a piercing member mounted on said second canister, said piercing member constructed to pierce said frangible membrane covering said second opening defined through said first perimeter wall of said first canister;

said first and second canisters constructed to be mechanically connected to one another.

10. An apparatus for altering characteristics of a fluid in accordance with claim 9, wherein said first canister is constructed to be connected to a source of a fluid whereby fluid from said source can flow through said first opening defined by said first perimeter wall, and wherein said second canister is constructed to be connected to an apparatus for delivering fluid to a patient, whereby fluid can flow from a fluid source through said first and second internal chambers and into an apparatus for delivering fluid to a patient.

11. An apparatus for altering characteristics of a fluid in accordance with claim 9, said apparatus further comprising a spike constructed to be mounted on said first canister, said spike defining a channel therethrough for fluid communication with said first internal chamber through said first opening defined through said first perimeter wall.

12. An apparatus for altering characteristics of a fluid in accordance with claim 9, wherein at least one of said first internal chamber and said second internal chamber includes a transverse wall having at least one aperture therethrough to divide said at least one internal chamber into separate chamber portions.

* * * * *